United States Patent
Zoss et al.

(10) Patent No.: US 10,369,021 B2
(45) Date of Patent: Aug. 6, 2019

(54) POWERED ORTHOTIC SYSTEM FOR COOPERATIVE OVERGROUND REHABILITATION

(71) Applicant: Ekso Bionics, Inc., Richmond, CA (US)

(72) Inventors: Adam Zoss, Berkeley, CA (US); Tim Swift, Clovis, CA (US); Alec Berg, San Mateo, CA (US); Katherine Strausser, Berkeley, CA (US); Erick Brendan St. John, Pleasanton, CA (US)

(73) Assignee: Ekso Bionics, Inc., Richmond, CA (US)

( * ) Notice: Subject to any disclaimer, the term of this patent is extended or adjusted under 35 U.S.C. 154(b) by 727 days.

(21) Appl. No.: 14/776,485

(22) PCT Filed: Mar. 13, 2014

(86) PCT No.: PCT/US2014/025343
§ 371 (c)(1),
(2) Date: Sep. 14, 2015

(87) PCT Pub. No.: WO2014/159857
PCT Pub. Date: Oct. 2, 2014

(65) Prior Publication Data
US 2016/0030201 A1 Feb. 4, 2016

Related U.S. Application Data

(60) Provisional application No. 61/819,377, filed on May 3, 2013, provisional application No. 61/781,408, filed on Mar. 14, 2013.

(51) Int. Cl.
*A61H 3/00* (2006.01)
*A61F 2/68* (2006.01)
(Continued)

(52) U.S. Cl.
CPC ............... *A61F 2/68* (2013.01); *A61B 5/112* (2013.01); *A61B 5/1122* (2013.01);
(Continued)

(58) Field of Classification Search
CPC . A61F 2/68; A61F 5/0102; A61F 5/01; A61H 3/00; A61H 1/024; A61H 3/008;
(Continued)

(56) References Cited

U.S. PATENT DOCUMENTS 5,112,296 A 5/1992 Beard et al.
6,296,595 B1 10/2001 Stark et al.
(Continued)

FOREIGN PATENT DOCUMENTS

CN 101204347 6/2008
JP 2003150036 5/2003
(Continued)

OTHER PUBLICATIONS

Banala et al., "Robot Assisted Gait Training with Active Leg Exoskeleton", IEEE Transactions on Neutral Systems and Rehabilitation Engineering, vol. 17, No. 1, Feb. 2009.

*Primary Examiner* — Quang D Thanh
(74) *Attorney, Agent, or Firm* — Diederiks & Whitelaw, PLC.

(57) ABSTRACT

A powered orthotic system, such as an exoskeleton, is employed for overground rehabilitation purposes by adapting and adjusting to real-time needs in a rehabilitation situation whereby the system can be initially controlled to perform gait functions for a wearer based on a predetermined level of assistance but the predetermined level of assistance can be varied, based on one or more rehabilitation parameters or specific needs of the wearer undergoing therapy, through the application and adjustment of appropriate variables associated with operation of the system.

20 Claims, 5 Drawing Sheets

(51) Int. Cl.
  *A61F 5/01* (2006.01)
  *A61B 5/11* (2006.01)
  *A61B 5/00* (2006.01)
  *A61H 1/02* (2006.01)

(52) U.S. Cl.
  CPC .......... *A61B 5/4836* (2013.01); *A61B 5/4851* (2013.01); *A61B 5/6811* (2013.01); *A61F 5/01* (2013.01); *A61F 5/0102* (2013.01); *A61H 1/024* (2013.01); *A61H 3/00* (2013.01); *A61H 3/008* (2013.01); *A61H 2003/007* (2013.01); *A61H 2201/165* (2013.01); *A61H 2201/5007* (2013.01); *A61H 2201/5061* (2013.01); *A61H 2201/5069* (2013.01)

(58) Field of Classification Search
  CPC .... A61H 2201/5007; A61H 2201/5061; A61H 2201/5069; A61B 5/112; A61B 5/4836; A61B 5/6811; A61B 5/1122; A61B 5/4851
  See application file for complete search history.

(56) References Cited

U.S. PATENT DOCUMENTS

| | | | |
|---|---|---|---|
| 6,966,882 | B2 | 11/2005 | Horst |
| 7,066,896 | B1 | 6/2006 | Kiselik |
| 7,190,141 | B1 | 3/2007 | Ashrafiuon et al. |
| 7,774,177 | B2 | 8/2010 | Dariush |
| 8,034,005 | B2 | 10/2011 | Yasuhara et al. |
| 8,048,007 | B2 | 11/2011 | Roy |
| 8,052,629 | B2 | 11/2011 | Smith et al. |
| 8,142,370 | B2 | 3/2012 | Weinberg et al. |
| 8,147,436 | B2 | 4/2012 | Agrawal et al. |
| 8,529,477 | B2 | 9/2013 | Wall, III et al. |
| 8,545,420 | B2 | 10/2013 | Einav et al. |
| 8,556,836 | B2 | 10/2013 | Menga |
| 8,574,174 | B2 | 11/2013 | Sankai |
| 2004/0122483 | A1 | 6/2004 | Nathan et al. |
| 2005/0010150 | A1 | 1/2005 | Firsov |
| 2005/0101887 | A1 | 5/2005 | Stark et al. |
| 2005/0245853 | A1 | 11/2005 | Scorvo |
| 2006/0282017 | A1 | 12/2006 | Avni et al. |
| 2007/0016116 | A1 | 1/2007 | Reinkensmeyer et al. |
| 2008/0097269 | A1 | 4/2008 | Weinberg et al. |
| 2008/0108918 | A1 | 5/2008 | Joutras et al. |
| 2009/0036804 | A1 | 2/2009 | Horst |
| 2009/0171469 | A1 | 7/2009 | Thorsteinsson et al. |
| 2009/0306548 | A1 | 12/2009 | Bhugra et al. |
| 2010/0113980 | A1* | 5/2010 | Herr .................. A61F 2/60 600/587 |
| 2010/0318006 | A1 | 12/2010 | Horst |
| 2011/0105966 | A1 | 5/2011 | Kazerooni et al. |
| 2011/0105969 | A1 | 5/2011 | Nace |
| 2011/0295384 | A1* | 12/2011 | Herr .................. A61F 2/6607 623/24 |
| 2012/0004736 | A1* | 1/2012 | Goldfarb ............ A61F 2/60 623/25 |
| 2012/0165704 | A1 | 6/2012 | Kang et al. |
| 2012/0215140 | A1 | 8/2012 | Hirata et al. |
| 2012/0226203 | A1 | 9/2012 | Nakashima et al. |
| 2013/0102935 | A1 | 4/2013 | Kazerooni et al. |
| 2013/0226048 | A1 | 8/2013 | Unluhisarcikli et al. |
| 2013/0289452 | A1 | 10/2013 | Smith et al. |

FOREIGN PATENT DOCUMENTS

| | | |
|---|---|---|
| JP | 2011177329 | 9/2011 |
| JP | 2012145594 | 8/2012 |
| WO | WO 2007/038888 | 4/2007 |
| WO | WO 2012/048123 | 4/2012 |

\* cited by examiner

- Toe location
- Desired toe location
- Force applied by exoskeleton for a given toe locaiton

POWERED ORTHOTIC SYSTEM FOR COOPERATIVE OVERGROUND REHABILITATION

CROSS-REFERENCE TO RELATED APPLICATION

The present application represents a National Stage application of PCT/US2014/025343 entitled "Powered Orthotic System for Cooperative Overground Rehabilitation" filed Mar. 13, 2014, pending, which claims the benefit of U.S. Provisional Application Ser. No. 61/781,408 filed Mar. 14, 2013 entitled "Powered Orthotic System for Overground Rehabilitation" and U.S. Provisional Application Ser. No. 61/819,377 filed May 3, 2013 entitled "Methods of Control Modulation for Rehabilitation Through Powered Lower Extremity Orthotics."

STATEMENT REGARDING FEDERALLY SPONSORED RESEARCH OR DEVELOPMENT

This invention was made with U.S. government support under NSF Grant Nos. 0924037 and 1248509. The U.S. government has certain rights in the invention.

BACKGROUND OF THE INVENTION

The last decade has seen significant research into robotic rehabilitation devices, primarily due to the significant patient populations and the associated costs of care. For example, 610,000 people in the U.S. experience a first-time stroke annually. The total cost of care, including direct and indirect costs, associated with the stroke population in the U.S. in 2010 was estimated at $53.9 billion. While not all these costs are due to an impaired gait, a significant percentage of stroke survivors have mobility impairments that affect their quality of life. For ischemic strokes, which represent 83% of all strokes, survivors face significant lasting impairments: six months after discharge, 50% exhibited hemiparesis, 30% required assistance to walk, 26% were in nursing homes, and 26% were in assisted-living centers.

A number of treadmill-based robotic rehabilitation devices have been developed to assist with the gait rehabilitation process for these patients with an impaired gait. Some of these have even emerged as commercial devices that are deployed in rehabilitation facilities. The current commercial leader in robotic-assisted gait rehabilitation is the LOKOMAT, developed by Hocoma. This device is a stationary Body Weight Support Treadmill (BWST) system with actuated hips and knees in the sagittal plane, as well as actuated forward/back pelvis motion. The system, which is large and stationary, is currently in use in a few large research hospitals across the country that can afford to purchase the device and sacrifice the space to house it. LOKOMAT researchers have put significant effort into making up for the biofeedback to the user that is lost by not walking in the real world by creating simulated environments and presenting feedback scores to the user. Other research efforts into similar technologies have sought to further extend the point to which the user imitates overground walking. One device is LOPES from the University of Twente, which includes full pelvic positioning in the forward/back and right/left directions as seen in overground walking. Another is ALEX from the University of Delaware that completely frees one leg of the user to better simulate overground walking for subjects with single leg impairments, such as stroke patients.

These systems have numerous drawbacks however. Nearly all approaches to date have been stationary devices where body weight is supported by a frame, and a treadmill device simulates overground motion. Motion of the treadmill forces lower extremity motion, even if the patient is trying not to move. The walking motion promoted by such systems bears only superficial resemblance to walking motion required in the real world. The patient is thus forced to further learn a different set of skills and abilities to operate in the normal real world environment after therapy with one of the stationary systems.

The invention addresses the need for a system which can provide therapeutic assistance that facilitates development of the muscular and neurological capabilities necessary for subsequent unassisted coping with real-world situations, and overcomes the shortcomings of the previous approaches.

SUMMARY OF THE INVENTION

In order to overcome the limitations of the previous approaches, the inventive system described below has been developed. In particular, the combination of elements offers unique and novel benefits for the solution to problems encountered in gait assistance by powered orthotics.

Advances in mobile untethered exoskeletons have led to a new class of assistive devices that provide rehabilitation assistance while walking overground. These systems do not rely on overhead body weight support and are not confined to treadmills; instead, such systems allow the user's skeleton to support their bodyweight. One such device in this class is called EKSO™, which is developed by Ekso Bionics. EKSO™ has sagittal-plane actuation at the hip and knee joints of both legs and works by moving the joints through a walking gait. It is controlled by following position-based trajectories at the joints to generate the desired walking motion.

The EKSO™ system draws on a range of control strategies and control dimensions to adapt the operation of the assistive system to provide the most effective rehabilitation experience. The identification and adaptation of the particular strategies and dimensions, and the ways in which the adaptation occurs is a major portion of the inventive novelty of the EKSO™ system.

Of particular value is the ability to adapt the system to the needs of the individual in a dynamic fashion during use of the system, rather than setting system parameters that remain constant during use as is done in other approaches.

The invention sets forth methods of varying the assistance provided by the exoskeleton to the person. Further disclosed are methods for enabling the person to recover their balance, as are methods for aiding the therapist in controlling the exoskeleton.

To supplement overall concepts of overground robotic rehabilitation, this invention focuses on key control concepts to maximize the rehabilitation aspect. Specifically, this invention covers the concept of being able to vary the assistance of the robotic device to adapt it for what is best for the patient's current level rehabilitation. Early on in rehabilitation, a weak patient needs significant support just to stand up and walk. However, as the patient strengthens and gains coordination, the rehabilitation device should reduce its assistance to force the patient to continue to improve and maximize the rehabilitation efforts. Also included are key supporting concepts developed concurrently with the variable assistance algorithms.

DETAILED DESCRIPTION OF THE INVENTION

Figure 1:
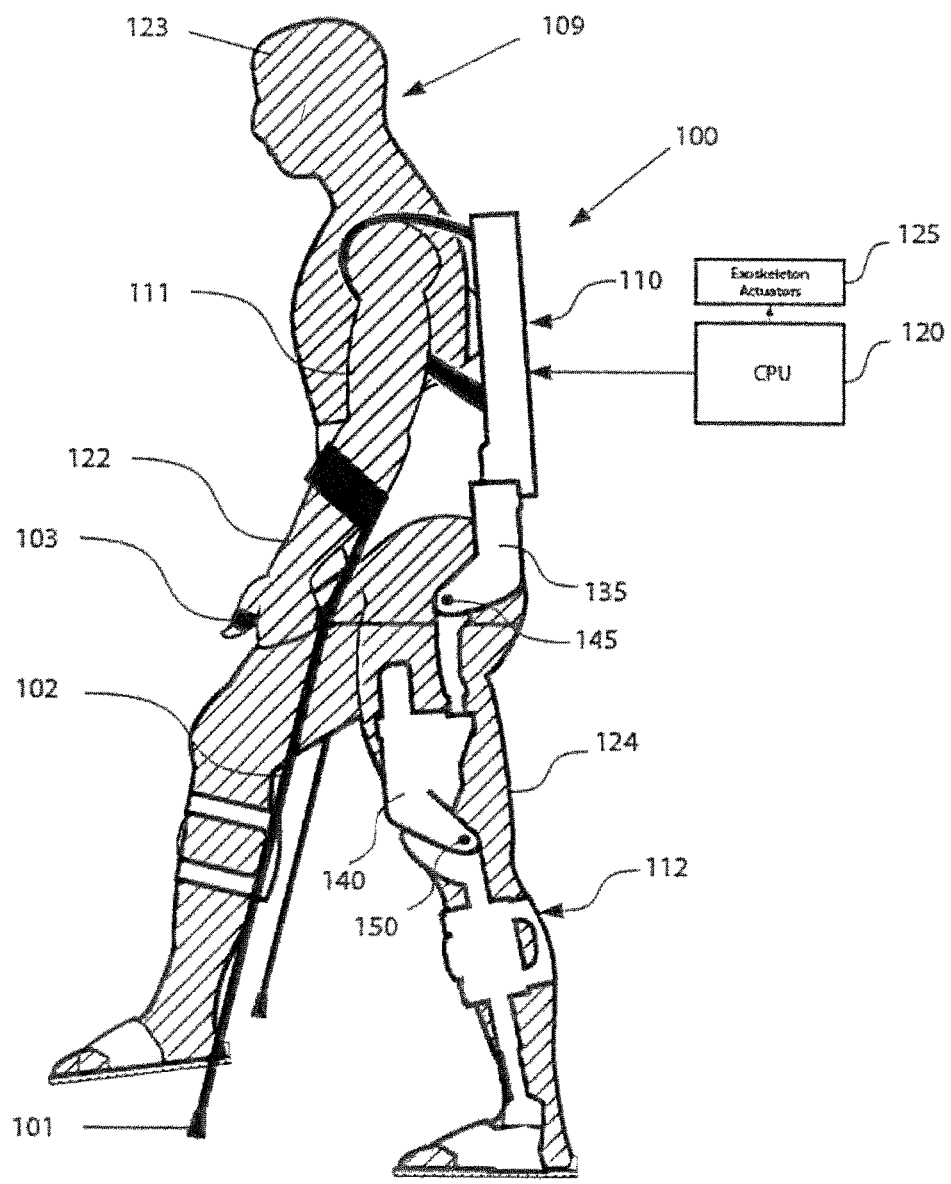
FIG. 1 is a side view illustrating a person wearing an exoskeleton employing the invention.

With reference to FIG. 1, an exoskeleton 100 having a trunk portion 110 and lower leg supports 112 is used in combination with a walking aid 102 (depicted as a forearm crutch in the figure), including a lower, ground engaging tip 101 and a handle 103, by a person or wearer 109 to walk. The wearer 109 is shown to have an upper arm 111, a lower arm (forearm) 122, a head 123 and lower limbs 124. In a manner known in the art, trunk portion 110 is configurable to be coupled to an upper body (not separately labeled) of the wearer 109, the leg supports 112 are configurable to be coupled to the lower limbs 124 of the person 109 and actuators, generically indicated at 125 but actually interposed between portions of the leg supports 112 as well as between the leg supports 112 and trunk portion 110 in a manner widely known in the art, for shifting of the leg supports 112 relative to the trunk portion 110 to enable movement of the lower limbs 124 of the wearer 109. In some embodiments, trunk portion 110 may be quite small and comprise a pelvic link wrapping around the pelvis of wearer 109. In the example shown in FIG. 1, the exoskeleton actuators 125 are specifically shown as a hip actuator 135 which is used to move hip joint 145 in flexion and extension, and a knee actuator 140 which is used to move knee joint 150 in flexion and extension. The exoskeleton actuators 125 are controlled by CPU 120, with CPU 120 being a constituent of an exoskeleton control system, in a plurality of ways known to one skilled in the art of exoskeleton control, but also operating in accordance with the present invention as detailed below. Although not shown in FIG. 1, various sensors in communication with CPU 120 are provided so that CPU 120 may monitor the orientation of the device, wearer, and walking aids. Such sensors may include, without restriction, encoders, potentiometers, accelerometers, and gyroscopes. As the particular structure of the exoskeleton can take various forms, is known in the art and is not part of the present invention, it will not be detailed further herein.

Exoskeletons are increasingly becoming accepted as tools of gait therapy and rehabilitation for persons with lower extremity gait impairments. While there is enormous interest in restoring gait to people who will never be able to walk without an exoskeleton, there is also an increasing understanding that exoskeletons can play an important role in rehabilitating the gait of people who have the physiological capability to regain control of their limbs. As, no doubt, regenerative medicine progresses (e.g., stem cell treatments), an increasing proportion of the population will move from the first category to the second; from merely looking at the exoskeleton as a means of transportation to looking at it as a means to relearn to walk. The control of the exoskeleton required to achieve rehabilitation may simply be stated as starting with getting a person up and walking with the exoskeleton fully controlling the gait and then transitioning more and more of the effort from the exoskeleton to the person as they relearn the motor control required for walking and as they regain strength. Eventually, the person may be able to walk without the exoskeleton.

This invention provides key elements that have been lacking, or not properly applied in prior approaches. Notably, the lack of any ability to adapt and adjust to the real-time needs of the rehabilitation situation and to the needs of the individual undergoing therapy through application and adjustment of appropriate variables has greatly limited the effectiveness of therapeutic systems to date. This adaptation requires several components that combine in new and unobvious ways to provide a quality therapeutic experience. The preferred embodiment incorporates these components as well as novel control strategies appropriate to each particular situation.

It will be evident to one skilled in the art that some components will be more effective or useful at some times than others, and that not all components may be included in every variation of the preferred embodiment. Further, there may be various forms of one or more components that may be more suitable in one circumstance over another. However, the inclusion or exclusion of one or more components or selection of a particular implementation of a component or strategy should not be considered as limiting of the scope of this invention.

General Device Control Framework

Several control schemes to control exoskeletons are well documented in the literature; generally, the control effort is the force or torque applied by one or more of the exoskeleton actuators in order to keep a leg on a desired trajectory. The trajectory can be represented in Cartesian or Polar coordinates or the foot, ankle, or hip or in joint angle space (with axes of hip and knee angle). Cartesian or Polar coordinates could be defined relative to another point on the exoskeleton (i.e., the foot position relative to the hip or relative to the opposite foot) or could be defined as an absolute position relative to a fixed point on the ground. One skilled in the art will recognize that basic mathematical relationships can be used to convert between these and other similar coordinate spaces to use for the trajectory and control logic. While any of these coordinate spaces are appropriate for this invention, to limit redundancy all of our example embodiments will utilize joint angle space. However, this choice of a particular space or coordinate system should not be considered as limiting on the scope of the invention.

The controller effort is determined by the distance and direction of the actual leg position from the desired leg position on the trajectory. Generally, the controller will apply an effort to push the actual leg position back towards the desired path and apply greater effort at greater deviations from the desired leg position. Additionally, the controller effort is often divided into two components: a component tangential to the trajectory and a corrective component pointed at an angle towards the trajectory. This invention separates the control effort into tangential and corrective components, each with a magnitude and direction within the coordinate space. It is well understood in the art of control systems that a given force vector may be applied from a known location on a robotic link by geometrically decomposing the desired force into joint torques.

This invention focuses on how the control effort is determined from the desired trajectory and actual leg positions, but does not address how to create the desired leg trajectory.

There are several elements of the controller design that are useful in enabling overground cooperative gait rehabilitation. Elements of this invention include, but are not limited to the following items:

Tunnel: This describes a region around a desired assistance trajectory where the degree of assistance provided has a proportional relationship to the amount of deviation from the ideal trajectory. The relationship may be linear, polynomial, exponential, non-linear or other custom function, and may be adapted in real-time to suit needs.

Real Time Trajectories: The method adapts the cooperative strategies to real-time leg trajectories that are required in overground walking. This contrasts with existing methods that implement the cooperative methods based on pre-computed gait trajectories.

Desired Gait Speed: The method allows for a desired gait speed which is used to determine the amount of controller effort along the tangential direction.

Variable Assistance: The method allows for varying the amount of exoskeleton assistance to allow the exoskeleton to address the varying ability of the wearer during the rehabilitation process. The variable rehabilitation effort is based on therapist settings along with feedback from the user such as the user's balance, safety, or quality of gait. In contrast, existing rehabilitation applications do not vary the assist level with respect to the users balance and safety because the user is firmly grounded through a connection to the roof or ground. In a further variation on the preferred embodiment, it is desirable that the therapist does not choose a set value of assistance, but rather lets the exoskeleton help as little as necessary to get through the gait cycle.

Correction Angle: Typical corrective strategies for trajectory deviations apply corrective forces normal to the trajectory. In many instances, force application is more effective if it is applied at an angle other than normal. In particular circumstances, the angle of application may be dynamically modified and strategies for determining and applying corrective forces are part of the inventive adaptive assistance.

Tunnel Puncture: In certain circumstances, such as to prevent a fall, it may be desirable to allow a significant deviation from the desired trajectory. In such cases, suspension of the tunnel assistance function (tunnel puncture) may be permitted to, for instance, place a foot on the ground, rather than continuing with a stride.

Virtual Back Wall: In some instances, it is desirable to prevent the leg from ever slowing down too much or from coming to a complete stop. The back wall is a concept of a virtual wall that typically moves along behind the person's gait position. But, if the person's leg goes too slowly then the wall catches up and pushes the leg forward until it moves at the desired speed again.

Torque Coordination—adapting the cooperative strategies to the unique challenges of implemented cooperative rehabilitation on an ungrounded robotic system. A specific embodiment is the balancing of torques between the legs of the user to maintain safety and stability. In contrast, existing grounded devices often consider each leg independent of the other.

Stance Leg Rehabilitation—allowing for the application of cooperative rehabilitation assistance in the stance phases of the gait for propulsive motion without additional forces from the treadmill. In contrast, all existing attempts at cooperative rehabilitation have been implemented on a treadmill resulting in the cooperative algorithm cooperating with the treadmills propulsive forces and not those from the user.

Therapeutic Feedback: For the therapy to be successful, it is important for the therapist to understand how much work the exoskeleton and patient are doing. Several methods have been developed to provide such feedback as well as strategies for when and how to provide feedback.

Tunnel

To determine the magnitude of the corrective controller effort, the concept of a tunnel around the trajectory has been well established in the literature. The cross-sectional shape of the tunnel represents the relationship between error (the distance of the actual leg position from the desired trajectory) and control effort (joint torque). In simple variations, the relationship may be linear, but in some variations the relationship may be a polynomial form (control effort proportional to the square or higher power of error), or a power function where the exponent may not be an integer (i.e., $F \sim e^{0.7}$). In these versions of the preferred embodiment, there may also be terms contributing to the control effort that are a function of the derivative or integral of the error in order to improve the stability or tracking error; these terms are well understood in the art of control systems and will not be further discussed.

In some variations, the tunnel may have a bottom so that there is a deadband region around the trajectory where the person can track without receiving any force, and the width of this region could be adjustable by the physical therapist. In certain implementations of the preferred embodiment, the tunnel may be represented as a set of piecewise lineations. In other variations, the tunnel need not be symmetric about the trajectory; for example, there might be no wall at all in the direction of lifting the foot, so that the patient can always step higher if they want. In still further variations, the tunnel shape could change along the trajectory. For example, it might be determined that, for a class of patients, their gait should be more tightly controlled near toe off and heel strike; then the tunnel walls could be made steeper there, and less steep in midswing.

In the preferred embodiment, the therapist controls the behavior of the exoskeleton by adjusting the shape of the tunnel. This may be done by changing coefficients in the controller which changes how stiff the walls of the tunnel are—the higher the gain, the more forceful the response of the exoskeleton to restore the person to the path. This is useful because the therapist may wish to constrain patients with great walking difficulties so they stay close to the path, whereas they may want patients who are more advanced in their recovery to have more flexibility in how they walk. In some variations, a stiffer wall may also be achieved by increasing the maximum allowable force, or by increasing the order of the equation between error and force (e.g., moving from linear to quadratic), or by a combination of more than one of these techniques. Likewise, the therapist might be able to adjust the tunnel shape with a graphical interface, and specify the shape in several positions. The device could then produce a smooth tunnel from these discrete cross sections. In general, the therapist need not understand the exact mathematical implementation, but merely the effect of the value they are adjusting on the behavior of the exoskeleton.

Although discussed here in angle/angle coordinates, these same concepts generally apply to Cartesian (X-Y) space as well and the particular choices do not reflect limitations on the invention.

Real Time Trajectories

One of the primary components of existing cooperative rehabilitation methods is the use of offline calculated pre-defined trajectories. This approach has emerged as a viable option for BWST machines because the user's torso is located in a fixed position that does not change from step to step, as it is either supported from above or its position is actively controlled. These existing methods that rely on predefined trajectories also depend on a fixed or tightly controlled torso position. In the case of a mobile platform, the torso position of the user varies significantly from step to step. As a result, any predefined trajectory that is designed conservatively enough to accommodate poor postures will lead to excessive clearances during good postures.

Since the ultimate goal is to retrain people to a natural gait, training them to excessive clearance is counterproductive. The trajectories used to control the behavior of the robotic device must be actively generated based on the real-time feedback of the user's posture. As a result, to best meet the needs of a mobile platform with a cooperative rehabilitation method, it must be able to accommodate for an actively generated trajectory. A novel aspect of this invention is the development of strategies to create and adapt real time trajectories.

Many approaches can be used to actively generate the trajectories including but not limited to a gait phase based piecewise calculation, or an optimizing controller that maintains the user's balance. To accommodate the non-predefined trajectories, the method must not rely on future calculations of the trajectory to determine the behavior. One variation of this behavior is a method that makes an estimate of the future trajectory using the current position and models used to generate the trajectory.

With a pre-defined trajectory, the controller can determine the desired leg position by finding the point along the trajectory that is closest to the actual leg position. With an actively generated trajectory, there is not a fully defined path to find a closest point on, so a different method is necessary to determine the desired leg position.

In the preferred embodiment according to this invention, the controller uses previous trajectory positions and the current trajectory position to estimate forward, assuming that the trajectory will continue in the same direction at the same rate. Estimating the future path allows the controller to find the new desired leg position as the point on this future path closest to the actual leg position.

An additional variation can place a minimum and/or maximum limit on how much the new desired leg position moves from the previous desired leg position. A minimum limit would prevent the desired leg position from ever completely stopping during the gait, while a maximum limit would prevent the leg from stepping too quickly (which could happen at low assistance levels with a strong patient leg).

Desired Gait Speed

The direction of the tangential control effort is tangential to the desired leg trajectory at the desired leg position which has been well established in the literature. There are various methods for determining the magnitude of the tangential control effort in the literature. For this invention, we have created a time offset counter which keeps track of how much the leg is ahead or behind a specified desired gait speed. Every control cycle, the progression of the desired leg position is compared to the desired gait speed to adjust the time offset counter. The magnitude of the tangential control effort is calculated as a function of the time offset counter. This function may include a linear, squared, or other polynomial relationship as well as a constant offset. Additionally, the function may also contain the derivative and/or integral of the time offset counter. The preferred embodiment also uses a different function depending on the sign of the time offset counter.

The functional relation between the time offset counter and tangential control effort determines the amount of assistance the device provides in helping the leg through the step. Therefore, the various parameters of this function may be modified by the therapist to adjust the level of assistance.

The time offset counter and/or the tangential control effort can also be limited to stay within a specified range. This prevents the controller effort from becoming too large when the patient is excessively ahead or behind the desired gait speed.

Variable Assistance

The fundamental concept of any cooperative control strategy is to allow the user to deviate from a healthy motion and to provide only corrective assistance based on the extent of that deviation. As a result, patients who need no help to move through the desired trajectory will receive no assistance from the device. The concept of variable assistance is to allow the control effort provided by the device to be adjustable such as weak patients can get the significant assistance necessary to help them walk, while stronger patients get less assistance as needed to correct gait deficiencies. As discussed above, the control effort includes tangential and corrective components and the assistance level of both of these components can be adjusted independently and different for each leg. This allows the therapist the ability to adjust how tightly the device enforces a correct gait (with the corrective assistance level) and how much help is necessary to move the foot forward through the gait (with the tangential assistance level).

In existing BWST implementations, the assistance is maintained constant throughout the gait. This can be done because if the user ever requires more assistance than the device can provide, either due to stubbing the toe or not enough user strength, the device shuts off and locks the user in the current position so they hang safely from the body weight support. This is not an acceptable failure scenario in a mobile platform due to the obvious concerns of locking while walking. Until now, no BWST control strategies have provided alternative failure responses that would be acceptable for use on a mobile platform. In a mobile application, not all device postures present the same risks or benefits to the user. As a result, the inventive method varies the assistance profile based on the state of the user. One form of the preferred embodiment varies the assistance profile based on the safety risks the user is exposed to because falling is the biggest risk. The embodiment varies the assistance profile to allow the user less room to deviate when in a potentially unsafe state. One method to achieve this is with a balance classification score to rate the safety of a user's posture to vary the assistance level.

Other variations can include but are not limited to additional scoring methods based on the user's safety due to risks other than falls, or to a score of gait quality. In this last case, the device may measure the quality of the persons gait by comparing the joint angles to the desired trajectory and producing an overall score (for example the root mean squared of the error between the desired and actual trajectories). If the score is high, the machine may reduce the amount of assistance until the score falls to the minimum acceptable level. This level may be set by a therapist. Additional variations of the method can provide a fixed adaptation that adapts one time in the beginning of the session based on a training routine. Still other variations can implement the adaptation in a non-uniform manner such that it adjusts one side of the profile in a different manner than the other side.

Someone ordinarily skilled in the art will recognize that alternative methods may be applied to determine the amount and kind of assistance required and that alternative methods may be used to measure relevant factors without limiting the scope of the invention.

These variations could adapt the correction and/or tangential control gains depending on the situation. The preferred embodiment seeks to reduce the complexity of the system by always keeping the corrective control effort at maximum gains and allowing the therapist and system to vary the tangential assistance, thereby providing a good balance that enforces a correct gait at all times and reduces the amount of variation the system and therapist must keep track of.

In yet a further variation on the preferred embodiment, it is desirable that the therapist does not choose a set value of assistance, but rather lets the exoskeleton help as little as necessary to get through the gait cycle. This variation has obvious utility in letting the therapist spend less time adjusting the exoskeleton while allowing the exoskeleton to require the maximum work possible from the patient. In the simplest variation, the exoskeleton controller can reduce the gain Kp referred to above slowly until the quality of the gait degrades to the minimum acceptable level. In practice however, it is necessary to implement a more complex adaptation rule.

Based on experimentation, a good choice of parameters has been found to be a ?:
1. Rate of progress along the trajectory in time is compared with an ideal rate of progress.
   a. Moving faster generally reduces the assistance provided by the machine.
   b. Moving slower generally increases the assistance provided by the machine.
2. Tangential force along the path is taken into account. With large tangential forces pushing the leg forward, it is expected that the rate of progress is faster, so the assistance is biased towards increasing. Similarly with large negative tangential forces (resisting forward progress), the assistance is biased towards decreasing.
3. Distance between the present and desired locations is considered. If the first two metrics tend to decrease the assistance, the amount of decrease is scaled down with larger distances between the present and desired location.

Figure 2:
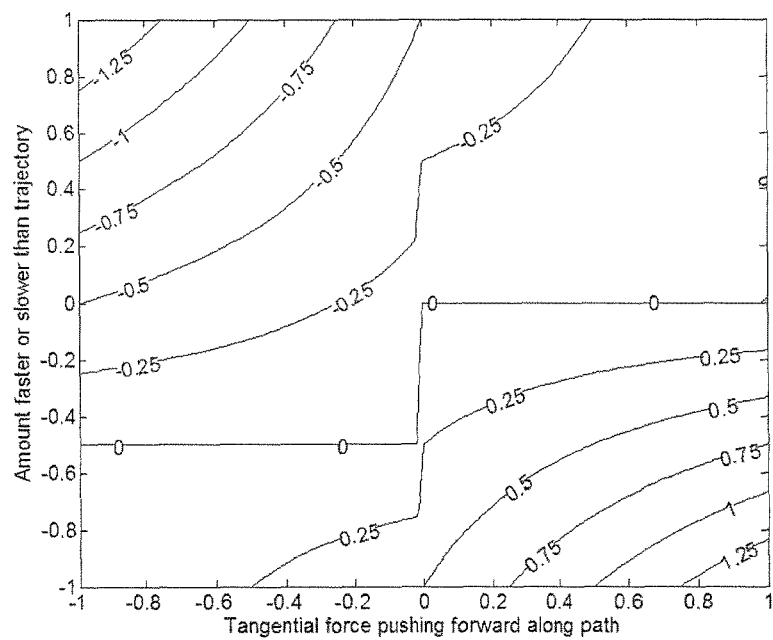
FIG. 2 graphically illustrates an adaptive assistance profile in accordance with the invention.

FIG. 2 graphically illustrates exoskeleton adaptation rules in accordance with the invention. The value reported in the contour plot is how much the assistance is raised (positive) or lowered (negative) as a function of the tangential force and speed of the limb relative to the trajectory (which are resealed before the adaptation and therefore do not have units). The adaptation is increased most quickly when the tangential force is large and positive and the person is very far behind the trajectory. In the preferred embodiment, assistance is increased and decreased by adjusting the proportional term (Kp) that relates assistance in the tangential direction to position error. In the preferred embodiment, the other controller gains (i.e., Kd or the derivative gain) are then scaled with Kp to keep the controller stable.

Someone ordinarily skilled in the art will recognize that alternative methods may be applied to estimate the needed control force vectors without limiting the scope of the invention. In the simplest form of the preferred embodiment, the estimated forces are simply the kinematic resultant of the joint torques applied by the exoskeleton, i.e., they do not account for the weight and dynamics of the exoskeleton links themselves. In other variations, however, the exoskeleton may estimate the forces between the exoskeleton and the human, either by directly measuring them, or by measuring the motion of the exoskeleton and estimating the dynamic effects of the exoskeleton, or by a combination of the two methods. This variation is more complex, but it allows for the forces to be applied to the person more accurately, and may be preferred when the exoskeleton will be used for patients with minimal gait deficiencies that require little correction.

In an alternative variation of the preferred embodiment, a baseline setting is provided so that the therapist can rescale the assistance provided by the exoskeleton. Because the exoskeleton does not, in general, know the weight or condition of the person, a greater level of assistance may be required for a heavier person even if they have more residual strength than a lighter person. This can be confusing. Providing a way to set a baseline for a patient and arbitrarily labeling that baseline 100% (or some other nominal value such as 1 or 10) and counting relative to that baseline can make the display simpler. The exoskeleton itself need not change the assistance provided, but rather it may simply rescale the display of assistance.

In one variation, the setting of the baseline may be automated. It has been found, by experimentation, that taking the maximum value of the tangential force over five steps provides a good baseline value (although the maximum of one step or ten steps or any convenient number would be a workable alternate embodiment). In practice, a therapist may simply press a button on the user interface, and the exoskeleton will then take the maximum of the last five steps and use this as a baseline. This is sometimes described as a "tare" function or "taring" the exoskeleton.

Correction Angle

Figure 3:
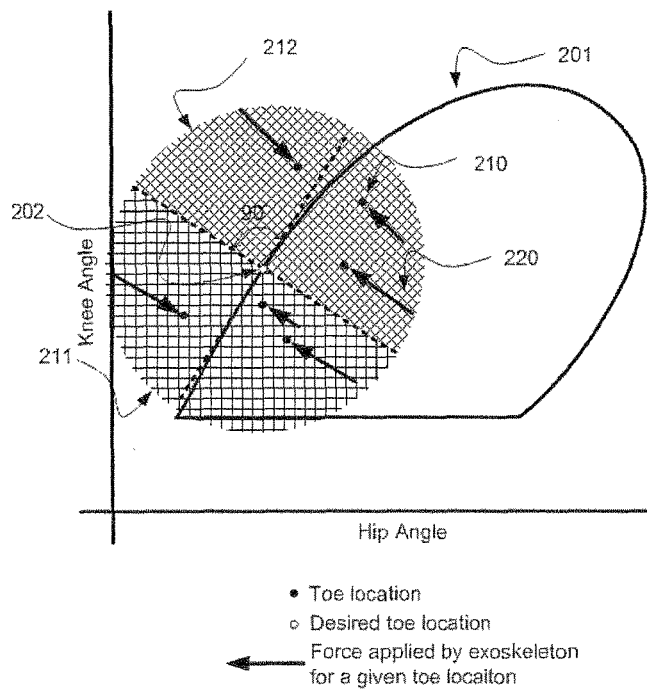
FIG. 3 is a behavior diagram for variable assist.

FIG. 3 diagrams a basic variable assist system behaving as discussed above. A trajectory for the toe, 201, is shown in parametric coordinates of hip/knee angle. Because the relative motion between the ankle and the toe is small compared to the leg overall, these techniques apply equally to tracking the ankle or any other point on the foot. The desired toe position is given by 202, and six hypothetical actual toe positions are indicated generally by 210, and the forces, 220, produced by the control system are also shown diagrammatically. The control system behaves essentially in the same manner regardless of whether the toe is ahead of the desired position (i.e., in region 212) or behind the desired position (region 211).

Figure 4:
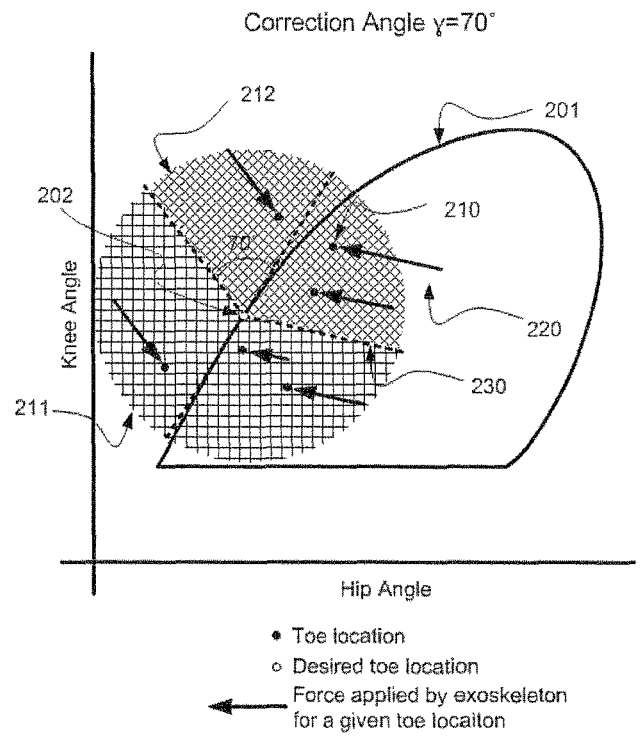
FIG. 4 is another behavior diagram for variable assist, particularly with generalized correction angle.

Through extensive experimentation, it was established that the state of the art did not adequately control the gait of the patient. A more general implementation was discovered and is illustrated in FIG. 4. If the regions 212 (in front of the present desired position) and 211 (behind the present desired position) are not held to be 90 degrees from the local tangent to the path, but rather by a correction angle gamma, the force for returning to the trajectory is parallel to this correction line (130). As the correction angle becomes very small, the person must move almost exactly along the path in order to make progress (since the corrective force will tend to drive them backwards along the path).

Figure 5:
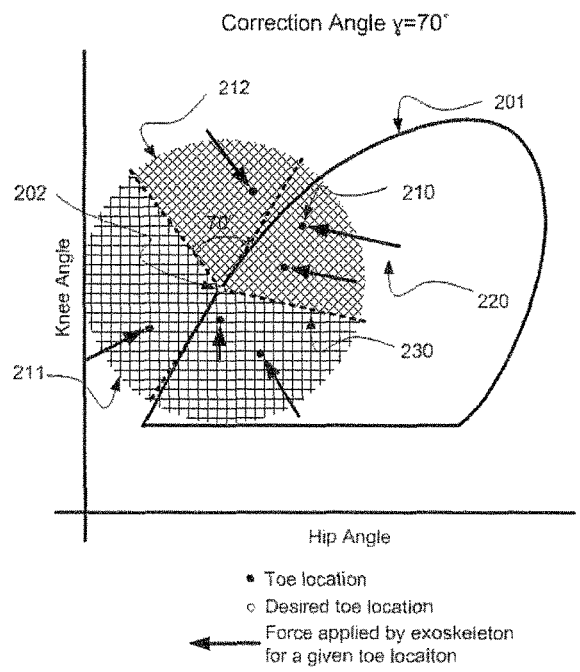
FIG. 5 is a further behavior diagram for variable assist, particularly with generalized correction angle and different behavior depending on location with respect to correction angle.

The preferred embodiment however, has a further improvement, diagrammed in FIG. 5. Here the angle of the force is different on either side of the correction line 230, with points in front of the correction line having a force applied parallel to the correction line and forces behind the correction line having forces applied in the direction of the desired position. The advantage of this variation is that when the patient is behind the desired location 202 they are given some assistance to reach it. Because of this assistance, they are less likely to move backwards, which is a problem associated with the method of FIG. 4. This improvement should also be combined with the variation where the desired target position is not allowed to move backwards along the trajectory for maximum effect. A correction angle of 70 degrees was discovered to be particularly effective. A correction angle of 90 degrees, which is similar to the method in FIG. 3, can allow for very sloppy walking. A patient with, for example, knee strength but little hip strength, could bend their knee in accordance with the desired trajectory and the exoskeleton would provide the work necessary to move the hip correctly. While this will accomplish the proximate act of stepping, it really does not facilitate the longer term goal of rehabilitation, which requires the patient to exercise what hip muscles they have. A correction angle in the order of 70 degrees will accomplish this by requiring some use of their hip muscles to progress. On the other end of the spectrum, it has been found experimentally that correction angles less than 45 degrees are sufficiently restrictive that even an able-bodied tester may not be able to walk while matching the desired trajectory so close every step.

Tunnel Puncture

A further problem of these systems is that the patient occasionally has difficulty balancing in the middle of the step and wants to put their foot back on the floor to stabilize themselves. All of the aforementioned systems would fight them until the end of the step where the path allows them to place their foot on the ground. Depending on the strength of the patient and the exoskeleton, the patient may not be able to overpower the exoskeleton mid-step and put their foot on the ground. This is alarming to the patient, and may be considered a hazard.

Figure 6:
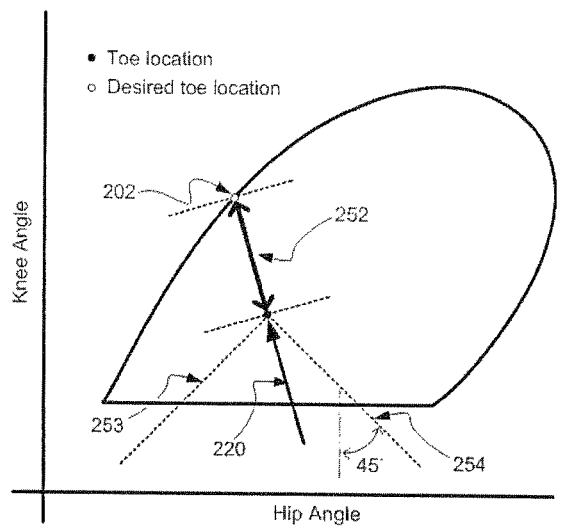
FIG. 6 is a behavior diagram for a tunnel puncture.

In one variation, when the knee angle error exceeds a maximum threshold, the controller recognizes that the patient is trying to put their foot back on the ground (since extending the knee is biomechanically how we put our feet on the ground). In the preferred embodiment, with reference to FIG. 6, the condition is more complicated: when force 220 is within 45 degrees of pointing up and distance error 252 is larger than a threshold, the controller recognizes that the patient is trying to put their foot back on the ground. Then the controller may place the foot back on the ground by transitioning to a mode that encourages the foot to go back to the ground, terminating the stepping action, changing the trajectory to rapidly intersect the ground, or any of a number of other equivalent methods.

In other variations, the angle might be larger, even 180 degrees, in which case the exoskeleton will abort the step if the error is simply too large. Obviously, a threshold on knee angle is only one potential method of detecting such an intent of the person. The controller could also put a threshold on distance in the vertical Cartesian axis, or on vertical force or knee torque (although for many of the controllers described above there is a one to one relation between force and position error, so with a rescaling of the threshold value, these conditions may be equivalent). Furthermore, the controller may take into account the time progressed through the step, or even construct a threshold that is a percentage of the knee angle so that the threshold itself is not constant. It will be noted that there are several methods available for accommodating unplanned patient actions, and selection of a particular method in an embodiment should not be construed as limiting of the inventive system.

Virtual Back Wall

In overground gait training, a difficulty arises when the person, either due to exhaustion or lack of muscle coordination, fails to make progress through a part of the swing cycle. In BWST, as discussed above, it is possible for the exoskeleton to simply stop; in overground gait training, stopping may leave the person in a configuration that is not statically stable and may not allow the therapist working with them to restore the device to a stable configuration. In these cases, the device needs to complete the swing trajectory for the person. This is often accomplished by the controller computing a virtual back wall that moves along the trajectory for the foot. The wall can be set to follow the person at a minimum rate through the swing trajectory, possibly after a delayed start and, should they cease forward progress, it will "catch up", forcing their foot along the path to ensure that the swing cycle is completed. In the preferred embodiment, the speed of the rear wall and/or the amount it delays before starting may be set by the therapist.

The amount of control effort from the back wall is a function of the distance between the back wall and desired leg position. The back wall control effort would be added to, and in the same direction, of the tangential control effort. The back wall control effort could be a linear, polynomial, or power function and could also include terms based on the derivative and/or integral of the distance from back wall to desired leg position.

The back wall concept can be implemented in conjunction with the device adjusting controller gains for undesirable situations as discussed above.

Torque Coordination

This type of overground device presents a distinctly new control problem from that of current state of the art BWST devices. These BWST devices easily coordinate the force on the foot with hip and knee joint torques because each leg is mechanically independent from the other leg. For these systems, the user's torso is grounded through the body weight support system and the hips of the device are grounded to the main structure. As a result, the system hardware presents the same issues as two independent two-link robotic manipulators.

In a mobile platform, however, the two legs are not independent because the only connection to ground is the stance foot. The preferred control method will coordinate the forces of the entire system to guarantee that one leg does not interfere with the other and that they do not make the user unstable.

One implementation of this concept is for the stance leg to control the torso angle instead of the hip angle. This guarantees torso stability at the expense of unknown hip motion. This implementation would require the above trajectory-based controllers to operate in different coordinate spaces during swing (hip and knee angle) and stance (torso and knee angle). Alternatively, the above control concepts could apply during swing, but not during stance.

Another variation of this force coordination is torque balancing from one hip to the other. A simple evaluation makes it clear that the rigid body of the user's torso will accelerate forward or backward if there is a torque imbalance reacting against it from the user's hips. As a result, the system must regulate the hip torque on a slave side of the system to be equal and opposite of the calculated torques of the other hip. Some other variations of this can include, but are not limited to, the hips regulating to a minimum difference between the two sides, neither hip being master and the overall output being scaled to regulate the magnitude of the calculated error, or extending beyond just hips to include other joints as well.

Mobile platforms also have more structural flexibility than traditional hardware because they have been optimized for size and weight reduction. This flexibility introduces another implementation issue not addressed with current BWST devices, which typically use large stiff legs. Therefore, in yet other variations, the structural flexibility of the mobile systems can be taken into account while computing the balancing forces referred to above. This may be done by estimating the torques generated by the device actuators or by directly measuring the loads on the device structure (for example, with strain gauges) or even measuring the human-machine or machine-environment interaction forces in order to better understand the deformation of the device structure.

Stance Leg Rehabilitation

A further aspect of the control method for a mobile platform is that assistance can be provided to the stance leg in a unique way. In existing rehabilitation devices, the stance leg is receiving assistance from the device but in a very different manner than overground walking. First, the stance leg is not fully loaded due to body weight support. Second, the leg is on a powered treadmill that introduces power to the stance leg because it moves relative to the fixed torso.

The overground platform allows the stance leg to be fully loaded by gravity and does not introduce any external power sources except for the motors directly at the joints. As a result, an implementation of the method exists that can provide cooperative rehabilitation assistance to the different actions of the stance leg including propulsive or supportive actions. In the preferred embodiment, the assistance profile (trajectories and coordinate spaces) for this phase of the gait can be different than that of the swing leg. This is anticipated because the stance leg is generally defined by high-torque and low-speed maneuvers. In other variations particular to stroke applications, the less affected leg may require support during stance to bear the weight of the exoskeleton. Because of these differences, separate parameters may be provided to the therapist to provide separate variable assistance responses during stance and swing.

This is not a problem associated with BWST because the exoskeleton is suspended from an external structure. In the simplest embodiment, the device may simply lock the stance leg knee. In more complex implementations, the device may calculate the torque that must be applied to the stance leg to counteract the weight of the device. In general, it is noted that the rehabilitation of a swing leg more closely resembles that of an upper extremity in that the limb is kinematically an open chain that is primarily concerned with motion in open space. The stance leg during walking, however, has a very different function, and the techniques of upper extremity rehabilitation and BWST are often not applicable. The stance leg may best be thought of as a weight bearing support, with the muscles around the knee stabilizing the leg and the hip muscle groups propelling the body. In this context, the strategies for overground rehabilitation focus on the exoskeleton producing a set of interaction forces over the stance leg that enforces these functions. In the preferred embodiment, the exoskeleton may directly measure the human-machine interaction forces in order to better reject disturbances from the exoskeleton. Existing literature for bipedal robotic walking uses target forces for the stance leg rather than position trajectories described above. The preferred embodiment utilizes similar balance and propulsion concepts to these bipedal stance forces and would be able to vary the assistance from these forces.

Therapeutic Feedback

Figure 7:
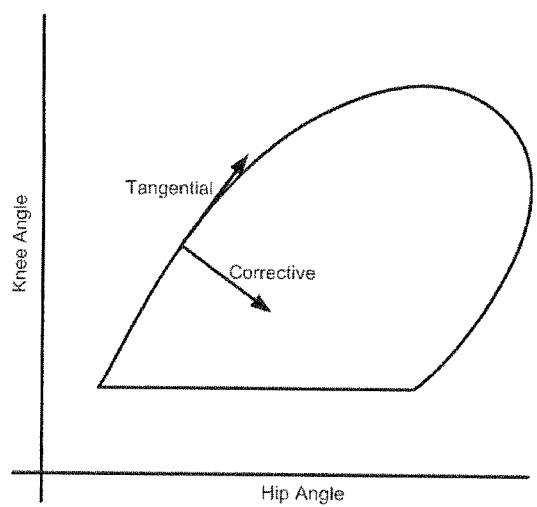
FIG. 7 is a behavior diagram based on tangential and corrective directions.

For the therapy to be successful, it is important for the therapist to understand how much work the exoskeleton and patient are doing. In the preferred embodiment, this estimate is done entirely in terms of the work done by the exoskeleton. With much experimentation, it has been established that it is best to present the therapist with separate measurements of the force needed to complete the step along the direction of the path (tangential feedback) and orthogonal to the path (corrective feedback); these directions are diagrammatically indicated in FIG. 7.

These estimates are generated by integrating the forces in the two directions according to the following formulae:

$$\text{Corrective Feedback} = \int_{Toe\ off}^{Heel\ Strike} (\text{Corrective Force}) * d(\%\ progress)$$

$$\text{Tangential Feedback} = \int_{Toe\ off}^{Heel\ Strike} (\text{Tangential Force}) * d(\%\ progress)$$

Where % progress is the percent of progress along the length of the path, HS is the point of heel strike when the swing cycle ends, and TO is toe off, when the swing cycle begins. It is important that the integral be with respect to progress and not time since the patient may pause during the gait cycle and the estimate is inaccurate if it continues to accumulate during this time. In essence, the estimate here is similar to a measurement of mechanical work done during the gait cycle.

In the preferred embodiment, the maximum of the tangential force over any one control cycle is recorded and displayed. It has been found that this maximum value is a good indication of the minimum level of assistance required for a given patient. Thus this can be used by the therapist as a calibration method—the therapist can walk the patient under full assistance, record the maximum value and reduce the assistance provided by the exoskeleton to that level.

In a variation of the preferred embodiment, further feedback is provided to prompt the therapist during the step if the patient is having difficulty. In this variation, the exoskeleton will provide a message describing what the person needs to do to complete the step. This is required because it is often not obvious by looking at the leg of the person and the exoskeleton which direction the person needs to move in order to come back to the trajectory.

Figure 8:
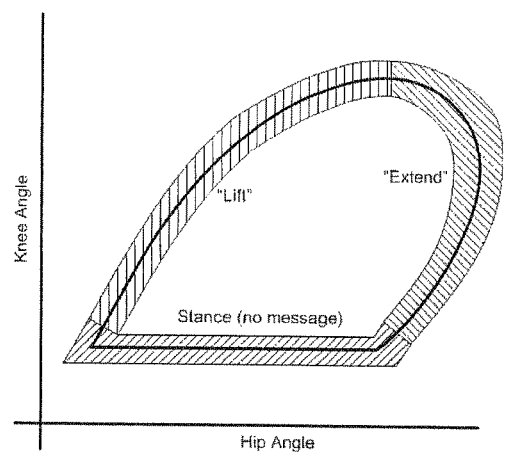
FIG. 8 is a behavior diagram based on lift/extend prompt.

In this variation, the message will be verbally or audibly generated by the exoskeleton. This message may also be text displayed to the user interface; in the simplest variation, the user interface simply gives the suggestions "lift" or "extend" depending on the direction that the patient needs to move their leg. Determining that the patient is having difficulty can be done by a variety of methods, such as when the corrective error becomes large or the leg fails to progress through the step at a minimum rate. FIG. 8 illustrates one method of determining what message to display. For instance, if it is detected that the patient is having difficulty, the exoskeleton chooses a message to display based on the position on the trajectory in parametric space. In some variations, feedback to the therapist may be required to inform the therapist when a patient has completed the step. Often a therapist's view may be obscured by the device and they may be unsure whether the patient's foot has reached the ground because the rate of travel through the step is not fixed. Therefore, the device may provide confirmation on the user interface or, in the preferred embodiment, with an audible tone.

Based on the above, it should be readily apparent that the present invention provides for performing overground rehabilitation for a wearer of a powered orthotic system which enables a predetermined level of assistance to be adaptively varied through numerous different control scenarios based on one or more rehabilitation parameters or specific needs, which can be sensed or inputted, of the wearer undergoing therapy, through the application and adjustment of appropriate variables associated with operation of the system. The system can be configured to automatically make adaptive modifications or the system operation can be altered through remote input, such as from the wearer or a rehabilitation therapist. In any case, although the invention has been described in terms of preferred embodiments with variations on particular elements, it will be recognized by someone ordinarily skilled in the art that various changes and/or modification can be made to suit the particular needs of a specific application. Similarly, other variations may be incorporated without altering or abridging the spirit of the invention.

The invention claimed is:

1. A method of performing overground rehabilitation for a wearer of a powered orthotic system comprising:
   initially establishing the powered orthotic system to perform gait functions for the wearer based on a predetermined level of assistance; and
   adaptively varying the predetermined level of assistance based on a rehabilitation parameter of the wearer, wherein:
   (1) the predetermined level of assistance is established by a desired assistance profile, adaptively varying the predetermined level of assistance includes creating a tunnel region around the desired assistance profile, and creating the tunnel region includes (a) defining a desired assistance trajectory, (b) defining one or more segments along said desired assistance trajectory, and (c) assigning to each of said one or more segments a function proportional to a distance from said desired assistance trajectory; or
   (2) varying the predetermined level of assistance includes providing a real-time trajectory, and providing the real-time trajectory includes (a) determining a previous position along a trajectory, (b) determining a current position along said trajectory, (c) determining a rate of progress along said trajectory, and (d) estimating, from said previous position, said current position and said rate, a future trajectory.

2. The method of claim 1, wherein the predetermined level of assistance is selectively varied by a rehabilitation therapist working with the wearer.

3. The method of claim 2, further comprising:
   estimating forces required for the wearer to complete at least one step of a gait cycle; and
   presenting an indicator based on the forces during the gait cycle to the rehabilitation therapist.

4. The method of claim 1, further comprising:
   sensing operational efforts by the wearer during use of the powered orthotic system; and
   varying the predetermined level of assistance based on the operational efforts.

5. The method of claim 1, further comprising:
   sensing operational movements during use of the powered orthotic system; and
   varying the predetermined level of assistance based on the operational movements.

6. The method of claim 1, wherein varying the predetermined level of assistance includes providing a desired gait speed, wherein providing the desired gait speed includes:
   (a) calculating a desired leg position based on the desired gait speed;
   (b) maintaining a time offset counter that is a difference between an actual leg position and the desired leg position; and
   (c) providing a tangential assistance that is a function of said time offset counter.

7. The method of claim 1, wherein varying the predetermined level of assistance includes providing a variable correction angle, wherein providing the variable correction angle includes:
   (a) determining an error between observed joint angles and desired joint angles along a trajectory;
   (b) computing from said error, a score; and
   (c) adjusting a level of assistance until said score falls to an acceptable level.

8. The method of claim 7, wherein the variable correction angle is not orthogonal to a trajectory of motion for the powered orthotic system, wherein the variable correction angle is less than 90 degrees and greater than or equal to 45 degrees to the trajectory of motion.

9. The method of claim 1, wherein varying the predetermined level of assistance includes dynamically modifying a desired trajectory, wherein dynamically modifying the desired trajectory includes:
   (a) identifying conditions where a significant deviation from the desired trajectory is appropriate;
   (b) determining when said conditions exist; and
   (c) modifying said desired trajectory according to a predetermined plan for responding to said conditions.

10. The method of claim 1, wherein varying the predetermined level of assistance includes providing leg rehabilitation assistance in stance phases of a gait cycle, wherein providing leg rehabilitation assistance in stance phases includes:
    (a) determining first forces required to stabilize a stance leg in accordance with a phase of motion;
    (b) measuring second forces applied to the powered orthotic system by the wearer;
    (c) computing third forces required to assist the wearer in stabilizing the stance leg based on the first and second forces; and
    (d) providing fourth, assistive forces by powering the orthotic system.

11. The method of claim 1, wherein the powered orthotic system includes an exoskeleton having: a torso portion configurable to be coupled to an upper body of the wearer; at least one leg support configurable to be coupled to a first lower limb of the wearer, with the at least one leg support including at least a thigh link rotatably connectable to the torso portion at a hip joint; a shank link rotatably connectable to the thigh link at a knee joint, said method further comprising: performing the gait functions through a first actuator for controlling motion of said hip joint, a second actuator for controlling motion of said knee joint, and a controller configured to control the first and second actuators with adaptive, variable levels of assistance in response to signals from a plurality of sensors for monitoring the exoskeleton.

12. The method of claim 1, wherein:
    the predetermined level of assistance is established by the desired assistance profile, adaptively varying the predetermined level of assistance includes creating the tunnel region around the desired assistance profile, and creating the tunnel region includes (a) defining the desired assistance trajectory, (b) defining the one or more segments along the desired assistance trajectory, and (c) assigning to each of the one or more segments the function proportional to the distance from the desired assistance trajectory; and adaptively varying the predetermined level of assistance includes providing a degree of assistance proportional to a distance of a current trajectory of the powered orthotic system from the desired assistance trajectory.

13. The method of claim 1, wherein:

varying the predetermined level of assistance includes providing the real-time trajectory, and providing the real-time trajectory includes (a) determining the previous position along the trajectory, (b) determining the current position along the trajectory, (c) determining the rate of progress along the trajectory, and (d) estimating, from the previous position, the current position and the rate, the future trajectory;

the trajectory is a current trajectory of the powered orthotic system; and estimating the future trajectory includes estimating a future position of the powered orthotic system along the current trajectory.

14. A method of performing overground rehabilitation for a wearer of a powered orthotic system comprising:

initially establishing the powered orthotic system to perform gait functions for the wearer based on a predetermined level of assistance; and adaptively varying the predetermined level of assistance based on a rehabilitation parameter of the wearer, wherein:

(1) varying the predetermined level of assistance includes establishing a virtual back wall, and establishing the virtual back wall includes (a) computing a trailing back wall which follows behind a trajectory of a path of the wearer, (b) allowing said trailing back wall to advance along said path even if when the wearer reduces or even ceases progress along said path, (c) identifying a condition when a position of said back wall is identical to a position of said wearer and (d) modifying an assistive force applied to said wearer to force continued motion along said path; or (2) varying the predetermined level of assistance includes coordinating torques between legs of the wearer, and coordinating the torques includes (a) identifying a condition of imbalance between hip joints of the powered orthotic system that results in adverse motion of a torso of the powered orthotic system, and (b) adjusting torsions in the hip joints to balances forces.

15. The method of claim 14, wherein:

varying the predetermined level of assistance includes establishing the virtual back wall, and establishing the virtual back wall includes (a) computing the trailing back wall which follows behind the trajectory of the path of the wearer, (b) allowing the trailing back wall to advance along the path even when the wearer reduces or even ceases progress along the path, (c) identifying the condition when the position of the back wall is identical to the position of the wearer, and (d) modifying the assistive force applied to the wearer to force continued motion along the path.

16. The method of claim 14, wherein:

varying the predetermined level of assistance includes coordinating the torques between the legs of the wearer, and coordinating the torques includes (a) identifying the condition of imbalance between the hip joints of the powered orthotic system that results in the adverse motion of the torso of the powered orthotic system, and (b) adjusting the torsions in the hip joints to balances the forces; and identifying the condition of imbalance includes identifying a condition of imbalance between the hip joints of the powered orthotic system that results in instability of the powered orthotic system.

17. An overground rehabilitative powered orthotic system including an exoskeleton comprising:

a torso portion configurable to be coupled to an upper body of a person;

at least one leg support configurable to be coupled to a first lower limb of the person, with the at least one leg support including at least a thigh link rotatably connectable to the torso portion at a hip joint, and a shank link rotatably connectable to the thigh link at a knee joint;

a first actuator for controlling motion of said hip joint;

a second actuator for controlling motion of said knee joint;

a plurality of sensors for monitoring the exoskeleton; and a controller configured to control the first and second actuators with adaptive, variable levels of assistance in response to signals from the plurality of sensors by initially establishing the exoskeleton to perform gait functions for the person based on a predetermined level of assistance and adaptively varying the predetermined level of assistance based on a rehabilitation parameter of the person, wherein:

(1) the controller is configured to (a) define a desired assistance trajectory, (b) define one or more segments along said desired assistance trajectory, and (c) assign to each of said one or more segments a function proportional to a distance from said desired assistance trajectory; or (2) the controller is configured to (a) determine a previous position along a trajectory, (b) determine a current position along said trajectory, (c) determine a rate of progress along said trajectory, and (d) estimate, from said previous position, said current position and said rate, a future trajectory.

18. The powered orthotic system of claim 17, further comprising: indicators for conveying operational parameters of the exoskeleton to a rehabilitation therapist, wherein the controller is configured to receive adaptive assistance signals from the rehabilitation therapist.

19. The powered orthotic system of claim 17, wherein:

the controller is configured to (a) define the desired assistance trajectory, (b) define the one or more segments along the desired assistance trajectory, and (c) assign to each of the one or more segments the function proportional to the distance from the desired assistance trajectory; and the controller is configured to control the first and second actuators to provide a degree of assistance proportional to a distance of a current trajectory of the exoskeleton from the desired assistance trajectory.

20. The powered orthotic system of claim 17, wherein:

the controller is configured to (a) determine the previous position along the trajectory, (b) determine the current position along the trajectory, (c) determine the rate of progress along the trajectory, and (d) estimate, from the previous position, the current position and the rate, the future trajectory;

the trajectory is a current trajectory of the exoskeleton; and the controller is configured to estimate, from the previous position, the current position and the rate, a future position of the exoskeleton along the current trajectory.

* * * * *